United States Patent
Model et al.

(10) Patent No.: US 11,406,321 B2
(45) Date of Patent: Aug. 9, 2022

(54) WEARABLE FLUIDIC SYSTEM FOR MEASURING SWEAT COMPOSITION

(71) Applicant: Epicore Biosystems, Inc., Cambridge, MA (US)

(72) Inventors: Jeffrey B. Model, Cambridge, MA (US); Roozbeh Ghaffari, Cambridge, MA (US); Alexander J. Aranyosi, Cambridge, MA (US); Stephen P. Lee, Cambridge, MA (US); Milan S. Raj, Cambridge, MA (US)

(73) Assignee: Epicore Biosystems, Inc., Cambridge, MA (US)

( * ) Notice: Subject to any disclaimer, the term of this patent is extended or adjusted under 35 U.S.C. 154(b) by 382 days.

(21) Appl. No.: 16/629,249

(22) PCT Filed: Jul. 24, 2018

(86) PCT No.: PCT/US2018/043430
§ 371 (c)(1),
(2) Date: Jan. 7, 2020

(87) PCT Pub. No.: WO2019/023195
PCT Pub. Date: Jan. 31, 2019

(65) Prior Publication Data
US 2020/0129112 A1    Apr. 30, 2020

Related U.S. Application Data

(60) Provisional application No. 62/536,462, filed on Jul. 25, 2017.

(51) Int. Cl.
*A61B 5/145*     (2006.01)
*A61B 5/00*      (2006.01)
(Continued)

(52) U.S. Cl.
CPC ............ *A61B 5/4266* (2013.01); *A61B 5/002* (2013.01); *A61B 5/0077* (2013.01);
(Continued)

(58) Field of Classification Search
CPC . A61B 5/1455; A61B 5/4266; A61B 5/14517; A61B 5/14532; A61B 5/6833
See application file for complete search history.

(56) References Cited

U.S. PATENT DOCUMENTS

| 2005/0106713 A1 | 5/2005 | Phan et al. |
| 2010/0063372 A1 | 3/2010 | Potts et al. |

(Continued)

OTHER PUBLICATIONS

Black, Robert E., et al. "Maternal and child undernutrition: global and regional exposures and health consequences." The Lancet, vol. 371, (2008), pp. 243-260.
Horton, Sue, et al. "Micronutrient Fortification (Iron and Salt Iodization)." Copenhagen Consensus Center Working Paper, Oct. 2008, pp. 1-32.
(Continued)

*Primary Examiner* — Marjan Fardanesh
(74) *Attorney, Agent, or Firm* — MacMillan, Sobanski & Todd, LLC

(57) ABSTRACT

A sweat sensing device includes a flexible body having a first, outwardly facing surface and a second, skin facing surface and a sweat channel formed in the body, the sweat channel having a first end defining a fluid inlet and a second end. A biochemical assay well formed in the sweat channel and an assay material is disposed in the biochemical assay well, the assay material positioned to react with sweat traveling through the sweat channel and to provide one of a visual indicator and an indicator detectable by a camera and connected processor of the flow of the sweat in the sweat channel.

9 Claims, 9 Drawing Sheets

(51) Int. Cl.
- *A61B 5/0205* (2006.01)
- *A61B 5/103* (2006.01)
- *G16H 20/00* (2018.01)
- *A61B 5/024* (2006.01)
- *A61B 10/00* (2006.01)

(52) U.S. Cl.
CPC ........ *A61B 5/02055* (2013.01); *A61B 5/1034* (2013.01); *A61B 5/14517* (2013.01); *A61B 5/14532* (2013.01); *A61B 5/14539* (2013.01); *A61B 5/14546* (2013.01); *A61B 5/6833* (2013.01); *A61B 5/746* (2013.01); *G16H 20/00* (2018.01); *A61B 5/024* (2013.01); *A61B 10/0064* (2013.01); *A61B 2562/164* (2013.01)

(56) References Cited

U.S. PATENT DOCUMENTS

2014/0323819 A1  10/2014  Hyde et al.
2015/0335288 A1  11/2015  Toth et al.

OTHER PUBLICATIONS

McIntire, Donald D., et al., "Neonatal Mortality and Morbidity Rates in Late Preterm Births Compared With Births at Term." Obstetrics & Gynecology, vol. 111, No. 1, (2008), pp. 35-41.

Barney et al., "Colorimetric Determination of Chloride with Mercuric Chloranilate", 1957, vol. 29, No. 8, pp. 1187-1188.

Nie et al., "A microfluidic device based on an evaporation-driven micropump", Biomed Microdevices, 2015, vol. 17, No. 47, pp. 1-12.

Koh et al., "A Soft, Wearable Microfluidic Device for the Capture, Storage, and Colorimetric Sensing of Sweat", Science Translational Medicine, 2016, vol. 8, No. 366, pp. 1-14.

"Sulfate (Colorimetric, Automated, Chloranilate)", 2017, p. 1, Retrieved Sep. 24, 2018, https//web.archive.org/web/20170121120052://www.epa.gov/sites/production/files/2015-12/documents/9035.

The extended European search report, Application No. 18839422.5, dated Apr. 19, 2021.

PCT International Search Report and Written Opinion, Application No. PCT/US18/43430, dated Oct. 15, 2018.

Japanese Office Action, Application No. 2020-527836, dated May 27, 2022.

WEARABLE FLUIDIC SYSTEM FOR MEASURING SWEAT COMPOSITION

BACKGROUND OF THE INVENTION

This invention relates in general to wearable fluidic systems for measuring and/or monitoring sweat rate, sweat composition, and/or biochemical information about one or more persons. In particular, this invention relates to an improved wearable sweat sensing device for use with an improved wearable sweat monitoring system for measuring and/or monitoring sweat rate, sweat composition, and/or biochemical information about one or more persons and using this information to provide feedback to a user of the wearable fluidic system, a coach, and/or a care provider.

Access to quantitative monitoring of electrolytes, micronutrients, chemical toxins, heavy metals, and metabolites for consumers, athletes, military personnel, firefighters, heart failure patients, kidney failure patients, diabetics, cystic fibrosis patients, mental health patients, preterm newborns, and others is critical to mitigate risks of dehydration, life threatening situations, and diseases, including sepsis, acidosis, anemia, hyperbilirubinemia, and dehydration.

Athletes, intensive care patients, and newborns are known to substantially benefit from sustained monitoring during daily living and sleep. For newborns, discharge from hospitals presents a daunting challenge for parents and communities that are entrusted with tracking nutrient deficits, fluid balance, and infant growth. Significant efforts to launch food programs and micronutrient fortified food aid for infants have helped address many life-threatening nutritional deficits facing fragile preterm newborns in the early weeks following delivery.

For athletes, military, and emergency personnel, monitoring the rate at which two fluids, electrolytes, and other essential body components are lost and consumed during exertion is essential for reducing the risk of injury or death due to dehydration, hyponatremia, or hypernatremia. In many cases the available tools for measuring these fluid body component losses are bulky and non-portable (e.g. scales for measuring body weight, and high performance liquid chromatography (HPLC) for measuring ionic composition). This limitation precludes the measurement of fluid losses at the most relevant times, i.e. when a person is still active.

Point-of-care wearable sensors have the potential to measure bioanalyte levels non-invasively, and could shift routine care and metabolite management from a laboratory or a hospital setting to remote field environments, or the home. Several forms of wearable, electronic, interstitial fluid and sweat analysis systems exploit electrochemical approaches for monitoring biomarker concentrations, but do not allow for collection, capture, or subsequent analysis of discrete samples of sweat at well-defined time points. Known methods rely on absorbent patches, for example, a PharmChek® sweat patch, or coiled tubes, for example, the Macroduct® sweat collection system, and serve only as passive vehicles for collecting sweat for post-hoc analysis. These conventional devices are expensive, bulky, heavy, unattractive aesthetically, and mechanically rigid. Thus, the conventional devices prevent intimate coupling with skin during physical exercise or intensive activity, exhibit poor signal quality, and physically disturb the user.

Thus, it would be desirable to provide an improved wearable sweat monitoring system having an improved wearable sweat sensing device that overcomes the limitations of conventional wearable sensors and that is high quality, low cost, is a component of an accessible health monitoring system that provides medical diagnostics needed to monitor athletes, patients, and newborns outside of the clinic. Access to quality medical diagnostics for these and other users could help reduce reliance on centralized care centers and provide health officials, parents, caregivers, sports teams, and coaches with better individual and demographic data for understanding treatment measures and outcomes.

SUMMARY OF THE INVENTION

This invention relates to a wearable sweat monitoring system and a sweat sensing device for use therewith that may include one or more fluidics sensors, a sweat volume collection channel, and colorimetric or electrochemical assays that detect a condition of a human subject, such as an athlete or patient, and relay this information to a coach, parent, caregiver, or other provider via smartphone.

A sweat sensing device includes a flexible body having a first, outwardly facing surface and a second, skin facing surface and a sweat channel formed in the body, the sweat channel having a first end defining a fluid inlet and a second end. A biochemical assay well formed in the sweat channel and an assay material is disposed in the biochemical assay well, the assay material positioned to react with sweat traveling through the sweat channel and to provide one of a visual indicator and an indicator detectable by a camera and connected processor of the flow of the sweat in the sweat channel.

In another embodiment, a sweat monitoring system includes a sweat sensing device configured to be adhered to the skin of a user to collect sweat and detect one of physiologic and a biometric condition selected from the group consisting of sweat volume, sweat volume loss, sweat rate, sweat chloride loss, sweat sodium loss, sweat lactate loss, sweat electrolyte loss, sweat metabolite loss, sweat pH, sweat glucose, and foreign chemical and toxin concentrations in the sweat. An interactive console station has a connected camera that captures an image of the sweat sensing device and generates an output to the user via the interactive console station.

Various aspects of this invention will become apparent to those skilled in the art from the following detailed description of the preferred embodiment, when read in light of the accompanying drawings.

DETAILED DESCRIPTION OF THE PREFERRED EMBODIMENT

Figure 1:
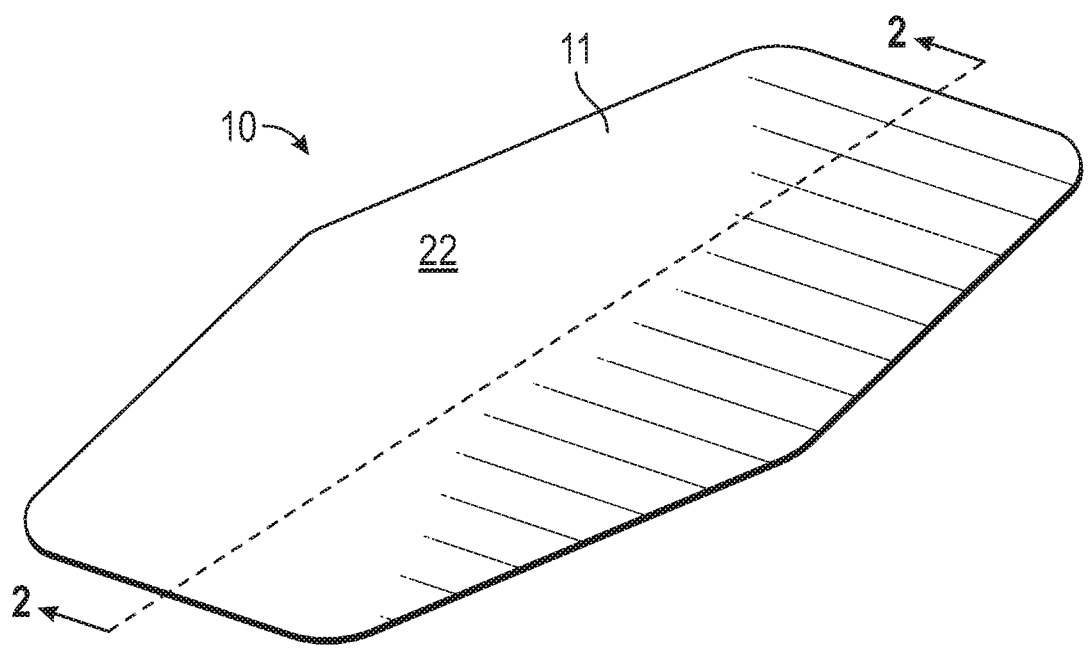
FIG. 1 is a perspective view of a first embodiment of a sweat sensing device in accordance with this invention.
Figure 2:
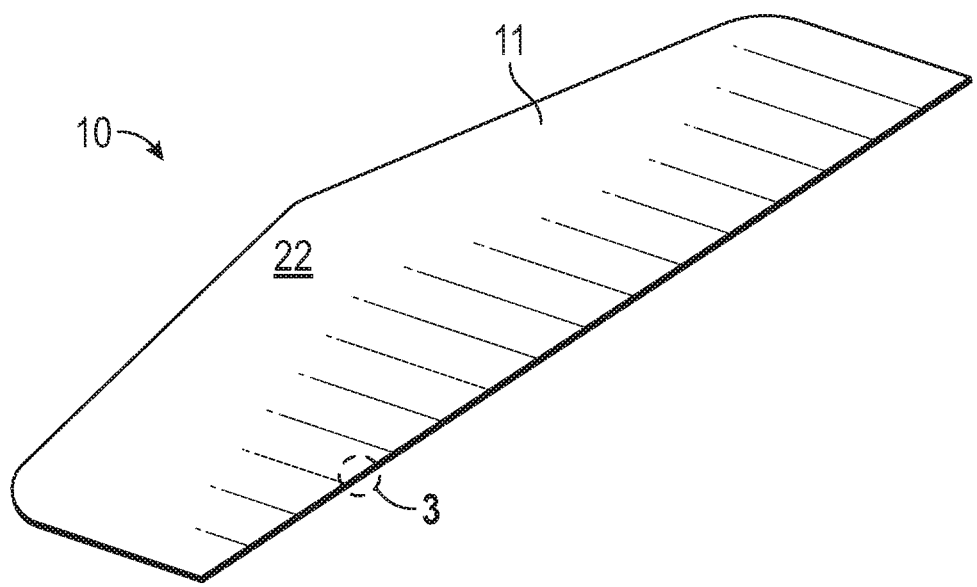
FIG. 2 is a cross-sectional view taken along the line 2-2 of FIG. 1.
Figure 3:
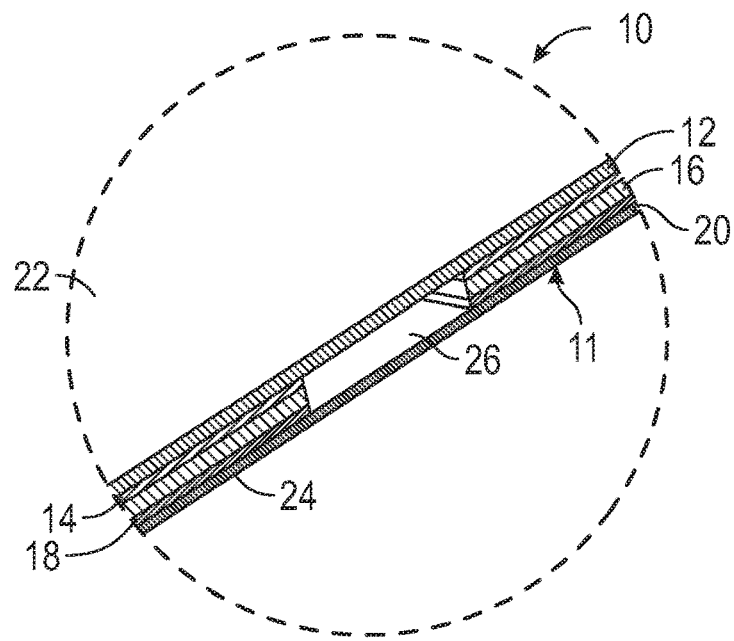
FIG. 3 is an enlarged cross-sectional view of the portion of the sweat sensing device within circle 3 of FIG. 2.

The present invention is directed to a wearable sweat sensing device and a sweat monitoring system that may sense sweat volume, sweat composition, and biochemical information from persons, such as athletes, patients, and newborns from one or more body locations in a clinical or an at-home environment. As described in detail below, the sweat monitoring system may relay information to the subject or other interested party in real time by analyzing images of fluid or sweat channels within the sweat sensing device with a camera, such as a smartphone camera or a camera connected to an interactive console station, e.g., a weighing station for athletes or a heart monitoring station. Processors within the smartphone or the interactive console station may analyze the image data to determine an output that defines an action to be taken, such as a recommendation of a specific formulation of electrolytes and fluids to consume to help achieve electrolyte balance, modify a real or a virtual environment, e.g., to alter a temperature or level of exertion, or to alert caregivers and/or emergency personnel. The recommended actions may be communicated to the user via the smartphone or the interactive console station.

Referring now to the drawings, there is illustrated in FIGS. 1 through 7 a first embodiment of a sweat sensing device 10 in accordance with this invention. The sweat sensing device 10 includes a substantially flexible body 11 having a first or upper layer 12, a second layer 14, a third layer 16, a fourth layer 18, and a fifth or lower layer 20. The upper layer 12 has a first or outwardly facing surface 22. The lower layer 20 has a second or skin facing surface 24. An adhesive is applied to the skin-facing surface 24, and the skin-facing surface 24 is covered by a removable adhesive liner 25 formed from any desired flexible and air/oxygen impermeable material.

The illustrated first layer 12 and the illustrated fifth layer 20 are formed from clear polyurethane having a thickness of about 0.004 inches. Alternatively, the first layer 12 and the fifth layer 20 may be formed from other desired soft, flexible, and clear material, such as silicone, polyethylene, polyethylene terephthalate (PET), or polyurethane. If desired, the fifth layer 20 may be formed from an opaque material. The first layer 12 and the fifth layer 20 may also have other desired thicknesses. For example, the first layer 12 may have a thickness within about 0.002 in to about 0.006 in, and the fifth layer 20 may have a thickness within about 0.001 in to about 0.004 in.

The illustrated third layer 16 is formed from clear silicone having a thickness of about 0.005 inches. Alternatively, the third layer 16 may be formed from other desired soft, flexible, and clear material, such as polyurethane, polyester, or PET, and may have other desired thicknesses, such as within about 0.004 in to about 0.006 in.

The illustrated second layer 14 and the illustrated fourth layer 18 are formed from clear acrylic PSA having a thickness of about 0.002 inches. The second and fourth layers 14 and 18 are adhesive layers that bond the first layer 12, the third layer 16, and the fifth layer 20 together. The material chosen for the adhesive second and fourth layers 14 and 16 may vary based on the material of the layers to which they are applied. For example, a silicon adhesive layer may be chosen to a bond silicon layers together. Alternatively, the second and fourth layers 14 and 18 may have other desired thicknesses, such as within about 0.001 in to about 0.004 in. If desired, the first layer 12, the third layer 16, and the fifth layer 20 may be directly bonded together by any conventional means, such as by ultrasonic welding.

One or more sweat channels may be formed in at least the third layer 16. As shown in embodiment of the sweat sensing device 10 illustrated in FIGS. 1 through 7, a first sweat channel 26 is formed in the third layer 16 and defines a serpentine pathway. Alternately, and as shown in the illustrated embodiment of the sweat sensing device 10, the first sweat channel 26 is also formed in the second and fourth layers 14 and 18, respectively. The first sweat channel 26 has a sweat inlet end 28 and a sweat outlet end 30 at a peripheral edge of the sweat sensing device 10 and positioned to allow sweat to exit the first sweat channel 26. The first sweat channel 26 may also include a biochemical assay well 32 near the sweat inlet end 28.

Additionally, a sweat channel may be formed such that portions of the sweat channel are variously formed in the second layer 14, the third layer 16, and in the fourth layer 18, or in combinations of layers, such as in the second and third layers 14 and 16 and in the third and fourth layers 16 and 18. Varying a height of the sweat channel throughout its length in this manner allows areas of greater sweat channel height to be positioned in the flexible body 11 as a visual indicator wherein a color change within the portions of the sweat channel having the greater height may be more easily seen because a larger volume of dye therein may appear darker in color.

When a sweat channel is formed having different heights throughout its length, i.e., when portions of the sweat channel are variously formed in the layers thereof, the sweat channel may crossover itself, allowing for a longer sweat channel without the need to increase the size of the sweat sensing device 10, 50, 70, 100, and 120.

Figure 4:
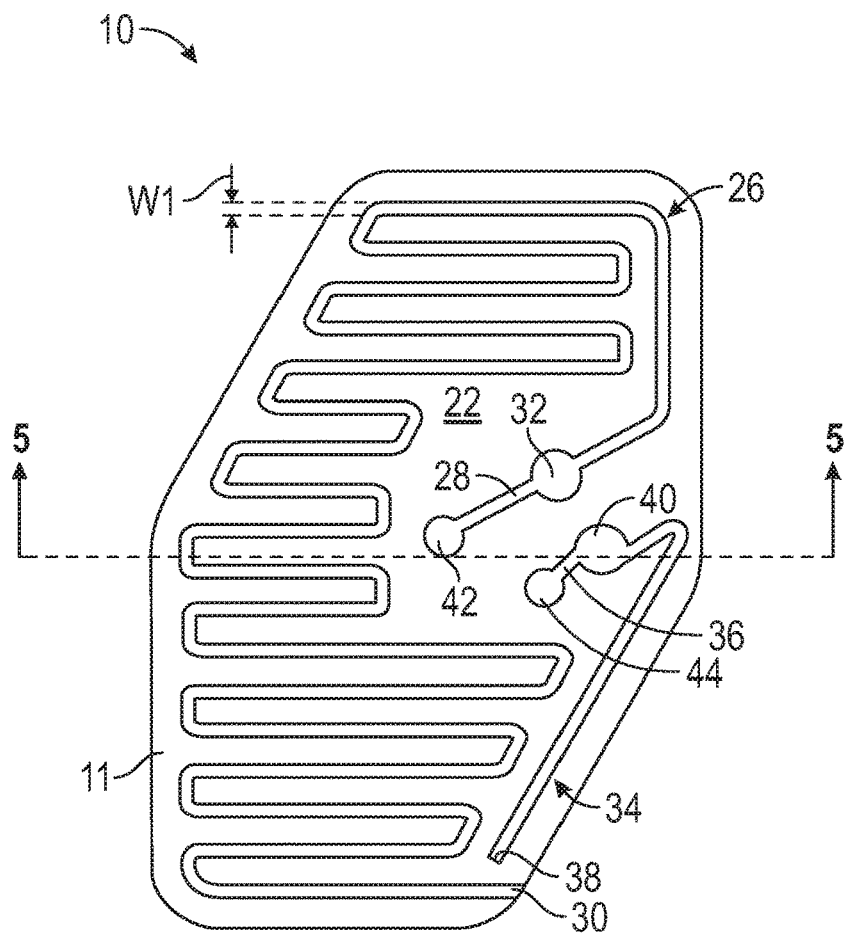
FIG. 4 is an alternate perspective view of the sweat sensing device illustrated in FIGS. 1 through 3.

As best shown in FIG. 4, a second sweat channel 34 is also formed in the second, third, and fourth layers 14, 16, and 18, respectively. The second sweat channel 34 has a sweat inlet end 36 and a second end 38 that, unlike the first sweat channel 26, does not define a sweat outlet. The second sweat channel 34 may also include a biochemical assay well 40 near the sweat inlet end 36.

The lower layer 20 may have fluid or sweat inlet ports in fluid communication with the sweat channels. As best shown in FIG. 4, the lower layer 20 includes a first sweat inlet port 42 in fluid communication with the first sweat channel 26, and a second sweat inlet port 44 in fluid communication with the second sweat channel 34. In the illustrated embodiment of the sweat sensing device 10, the biochemical assay wells 32 and 40 extend through the lower layer 20 to allow for the insertion a chemical assay therein.

Figure 5:
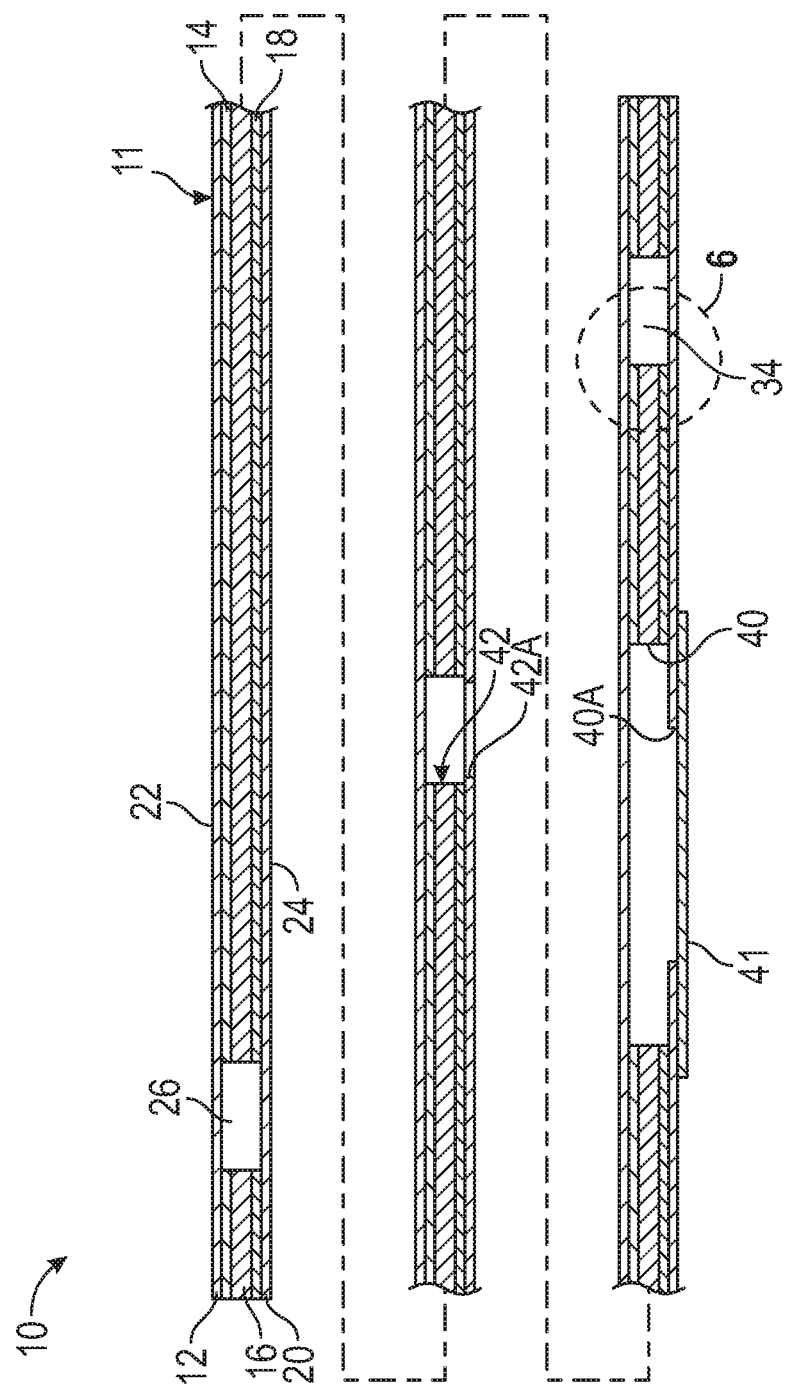
FIG. 5 is a cross-sectional view taken along the line 5-5 of FIG. 4.

As shown in FIG. 5, a portion 42A of the first sweat inlet port 42 in the lower layer 20 may be smaller than the portions of the first sweat inlet port 42 formed in the second, third, and fourth layers, 14, 16, and 18, respectively. Similarly, a portion 40A of the biochemical assay well 40, and a portion (not shown) of the biochemical assay well 32, in the lower layer 20 may be smaller than the portions of the biochemical assay wells 40 and 32 formed in the second, third, and fourth layers, 14, 16, and 18, respectively.

After the assay wells 32 and 40 are formed and the sweat sensing devices 10, 50, 70, 100, and 120 are assembled, a desired biochemical or chemical assay material, described in detail below, may be disposed therein. The assay wells 32 and 40 may then be closed with an adhesive layer 41, formed from any desired flexible material, such as the same material as the lower layer 20 to which the adhesive layer 41 is attached.

Figure 8:
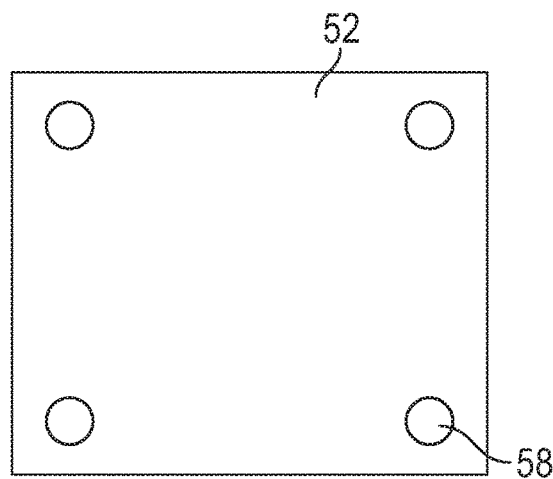
FIG. 8 is a plan view of a sheet or blank of material of an upper layer of a second embodiment of the sweat sensing device according to this invention.
Figure 9:
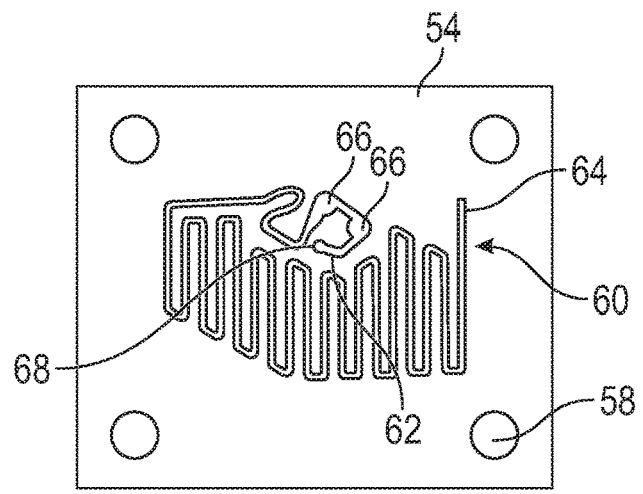
FIG. 9 is a plan view of a sheet or blank of material of one of an inner layer of the sweat sensing device illustrated in FIG. 8.
Figure 10:
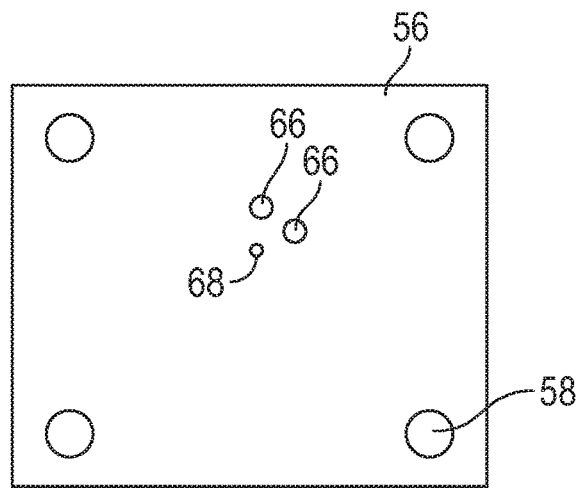
FIG. 10 is a plan view of a sheet or blank of material of a lower layer of the sweat sensing device illustrated in FIGS. 8 and 9.
Figure 11:
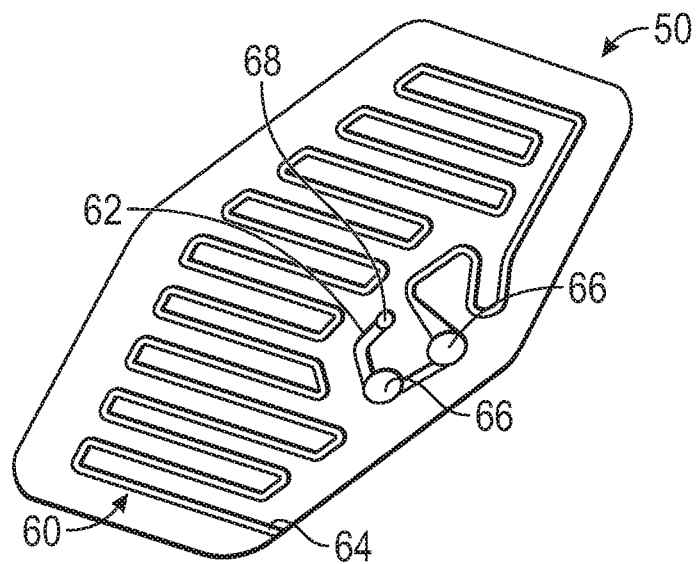
FIG. 11 a perspective view of the sweat sensing device formed from the layers illustrated in FIGS. 8 through 10.

The sweat channels and ports may be formed in the second, third, fourth, and fifth layers 14, 16, 18, and 20 by any desired means, such as with a laser, or die cut. For example, sheets or blanks of material comprising the layers of a second embodiment of a sweat sensing device 50 are shown in FIGS. 8 through 10. The assembled sweat sensing device 50 is also shown in FIG. 11. For example, FIG. 8 is a plan view of a sheet or blank of material of a first or upper layer 52 of the sweat sensing device 50. FIG. 9 is a plan view of a blank of material of one of an inner layer 54 of the sweat sensing device 50, such as any one of the second, third, fourth layers 14, 16, and 18 of the sweat sensing device 10 described above. FIG. 10 is a plan view of a blank of material of a lower layer 56 of the sweat sensing device 50. Each of the blanks 52, 54, and 56 include alignment holes 58 formed therein for aligning the blanks 52, 54, and 56 in a fixture, jig, or similar device (not shown).

As shown in FIG. 9, the inner layer 54 has a first sweat channel 60 formed therein. The first sweat channel 58 has a sweat inlet end 62 and a second end 64. The first sweat channel 58 may also include one or more biochemical assay wells 66 near the sweat inlet end 60.

The lower layer 56 may have a sweat inlet port in fluid communication with the sweat channel. As best shown in FIG. 10, the lower layer 56 includes a first sweat inlet port 68 in fluid communication with the first sweat channel 58. The one or more biochemical assay wells 66 extend through the lower layer 56.

It will be understood that a width W1 of the sweat channels, and a diameter of the assay wells, in the embodiments of the improved sweat sensing devices described herein may vary with the specific application of the sweat sensing device. The illustrated sweat channels 26, 34, and 60 may have any desired width W1, such as width of about 0.040 in. Alternatively, the sweat channels 26, 34, and 60 may have a width W1 within about 0.005 in to about 0.120 in. The inlet ports 42, 42, and 68 and the biochemical assay wells 32, 40, and 66 may have any desired diameter, such as a diameter of about 0.040 in and 0.160, respectively. Alternatively, the inlet ports 42, 42, and 68 may have a diameter of about 0.040 in to about 0.100 in, and the biochemical assay wells 32, 40, and 66 may have a diameter of about 0.020 in to about 0.200 in.

Although the illustrated inlet ports and assay wells are shown having a circular transverse section, the inlet ports and assay wells may be formed having other shapes, such as having a square transverse section, or other geometric shapes.

The biochemical assay wells 32 and 40 define colorimetric reaction sites that may be configured to react with very small, such as microliter volumes of sweat. The assay wells 32 and 40 may contain colored dyes, for example conventional food coloring dyes), chemical assays, fluoroscopic dyes, enzymatic assays, heavy metal assays, and protein/DNA based assays. In the sweat sensing device 10, one assay well 32 is formed in the sweat channel 26 and one assay well 40 is formed in the sweat channel 34. In the sweat sensing device 50, two assay wells 66 are formed in the sweat channel 60 near the sweat inlet port 68.

It will be understood that the sweat sensing devices disclosed herein, such as the sweat sensing devices 10, 50, and 70 (and the sweat sensing devices 100 and 120 described below), may be formed such that the depths of the sweat channels and/or the assay well vary. The color change induced by a chemical reaction will vary with a depth of the sweat channel or assay well according to the Beer-Lambert law. Measuring the color change in the sweat sensing devices 10, 50, 70, 100, and 120 at multiple depths may help reduce any negative effects related to lighting, exposure, and focus.

If desired, the outwardly facing surface 22 of the sweat sensing device 10 may be laminated with a very thin layer of polymer (not shown), such as a 25 µm layer of PET, having indicia printed thereon. The indicia may, for example, be aligned with the sweat channels 26 and/or 34 to highlight selected areas of the channels 26 and/or 34 for optical image capture.

The sweat sensing devices disclosed herein, such as the sweat sensing devices 10, 50, and 70 (and the sweat sensing devices 100 and 120 described below), may be used in a wearable sweat monitoring system 90, described in detail below and that analyzes sweat and applies the analysis to provide feedback to the user, patient, and/or caregiver, and to modify the operation or condition of one or more environments or systems. Advantageously, one or more people may be monitored by one or more sweat sensing devices 10, 50, 70, 100, and 120 that are configured to detect and indicate one or more physiologic or biometric condition of the person or persons to which they are attached. The conditions include, but are not limited to, sweat volume, sweat volume loss, sweat rate, sweat chloride loss, sweat sodium loss, sweat lactate loss, sweat electrolyte loss, sweat metabolite loss, sweat pH, sweat glucose, and foreign chemical and toxin concentrations in sweat.

Figure 15:
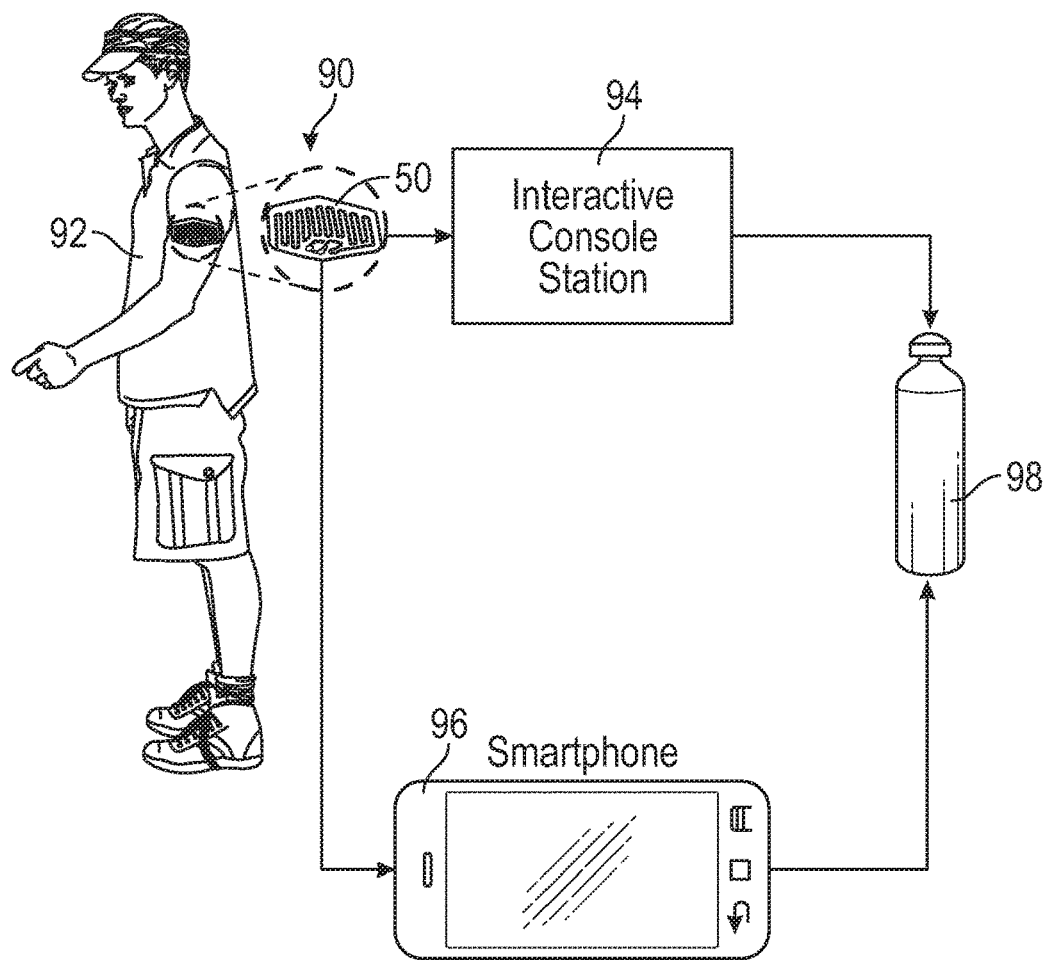
FIG. 15 is a diagram of a first embodiment of a wearable sweat monitoring system including the sweat sensing device according to this invention and showing flow of data through the wearable sweat monitoring system.

Referring now to FIG. 15, a diagram of the first embodiment of a wearable sweat monitoring system including the sweat sensing device 10, 50 according to this invention is shown at 90, and shows the flow of data therethrough. The wearable sweat monitoring system 90 is described in detail below and includes a person, such as an athlete 92 to whom a sweat sensing device, such as the sweat sensing device 50 has been affixed. The wearable sweat monitoring system 90 further includes an interactive console station 94 and/or a smartphone 96, and an output message 98, such as a recommendation to consume a specific formulation of electrolytes, such as a specific electrolyte replenishment beverage, carbohydrates, and fluids to consume to achieve electrolyte and metabolite balance in the user, a recommendation to consume specific nutrients, or a signal that modifies the operation or condition of one or more environments or systems.

If desired, the sweat channels, such as the sweat channels 26, 34, and/or 60 may have colored dye, such as red food coloring dye, deposited therein. In these embodiments, the sweat sensing devices 10, 50, and 70 are configured to measure sweat volume in the sweat channels 26, 34, and/or 60, and may be further configured to measure chloride concentration in the biochemical assay wells 32, 40, and 66. The sweat volume in the sweat channels 26, 34, and/or 60 may be displayed colorimetrically. The chloride concentration in the biochemical assay wells 32, 40, and 66 may be displayed thermochromically. For example, the indicia on the polymer laminate (not shown) applied to the outwardly facing surface 22 and described above may include an indicator of the chloride concentration level.

It has been shown that chloranilate will react with chloride in sweat. It has been further shown that the concentration of chlorine in the sweat present in the biochemical assay wells 32, 40, and 66 may be indicated by the shade of purple displayed therein. To assist in immobilizing the chloranilate in the biochemical assay wells 32, 40, and 66 and to prevent the chloranilate from flowing through the sweat channels 26, 34, and/or 60 during extended periods of storage, a gel, such as suspensions of p-HEMA or polyethylene glycol (PEG) may be added to the chloranilate in the biochemical assay wells 32, 40, and 66. Alternatively, the biochemical assay wells 32, 40, and 66 may contain dehydrated portions of colored dyes. The dehydrated colored dyes will then change color when mixed with sweat. If desired, other chemical assays may be used to test the sweat for other desired sweat conditions or parameters, such as blood glucose, lactic acid, and sweat volume.

This color and/or color change in the sweat channels 26, 34, and/or 60 and in the biochemical assay wells 32, 40, and 66 may then be viewed and assessed by the user, or measured and optionally quantified by an external device, such as the camera of the smartphone 96, a camera or other imaging device attached to the interactive console station 94, or other means of deriving a quantified measurement from a color and/or color change. Advantageously, the sweat sensing devices 10, 50, 70, 100, and 120 may be viewed and quantified by the user, or measured and optionally quantified by the external device in real-time while the sweat sensing device 10, 50, 70, 100, and 120 is on the user's body. This allows recommendations for nutrition, such as electrolyte replenishment and recommendations for environmental changes, as described in detail below, to be provided to the user while the user is still engaged in physical activity or has just completed the physical activity.

Figure 12:
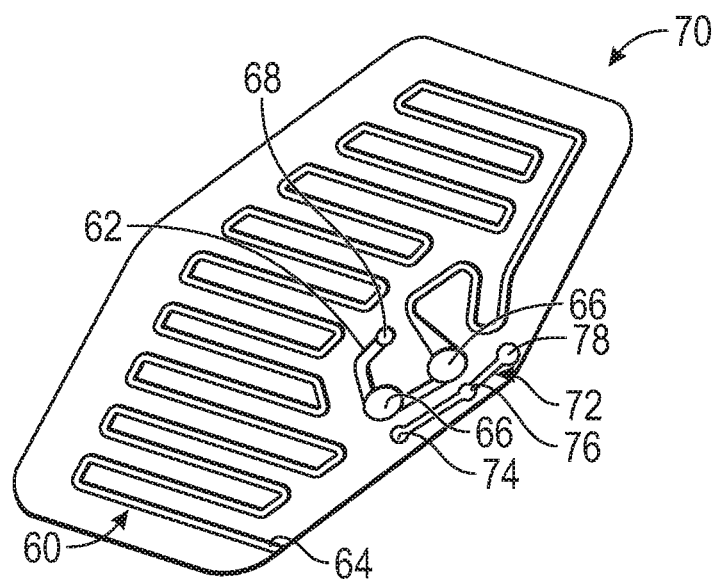
FIG. 12 a perspective view of a third embodiment of the sweat sensing device according to this invention.

A third embodiment of the sweat sensing device is shown at 70 in FIG. 12. The sweat sensing device 70 is similar to the sweat sensing device 50, but additionally includes a second sweat channel 72 configured to measure temperature. The second sweat channel 72 includes a second sweat inlet port 74 that extends through the lower layer 56 and is in fluid communication with the second sweat channel 72. A color viewing window 78 is formed at a distal end of the second sweat channel 72, and a chloranilate mixing well 76 is formed intermediate the second sweat inlet port 74 and the color viewing window 78. As described above, sweat may enter the second sweat channel 72 through the sweat inlet port 74 and travel to the chloranilate mixing well 76 where the sweat mixes with the chloranilate. The combined sweat and chloranilate my then travel within the sweat channel 72 to the color viewing window 78, wherein the sweat-chloranilate mixed has changed color in a manner detectable to the naked eye and/or an external device, such as the camera of the smartphone 96, a camera or other imaging device attached to the interactive console station 94, or other means of deriving a quantified measurement from a color and/or color change.

Figure 13:
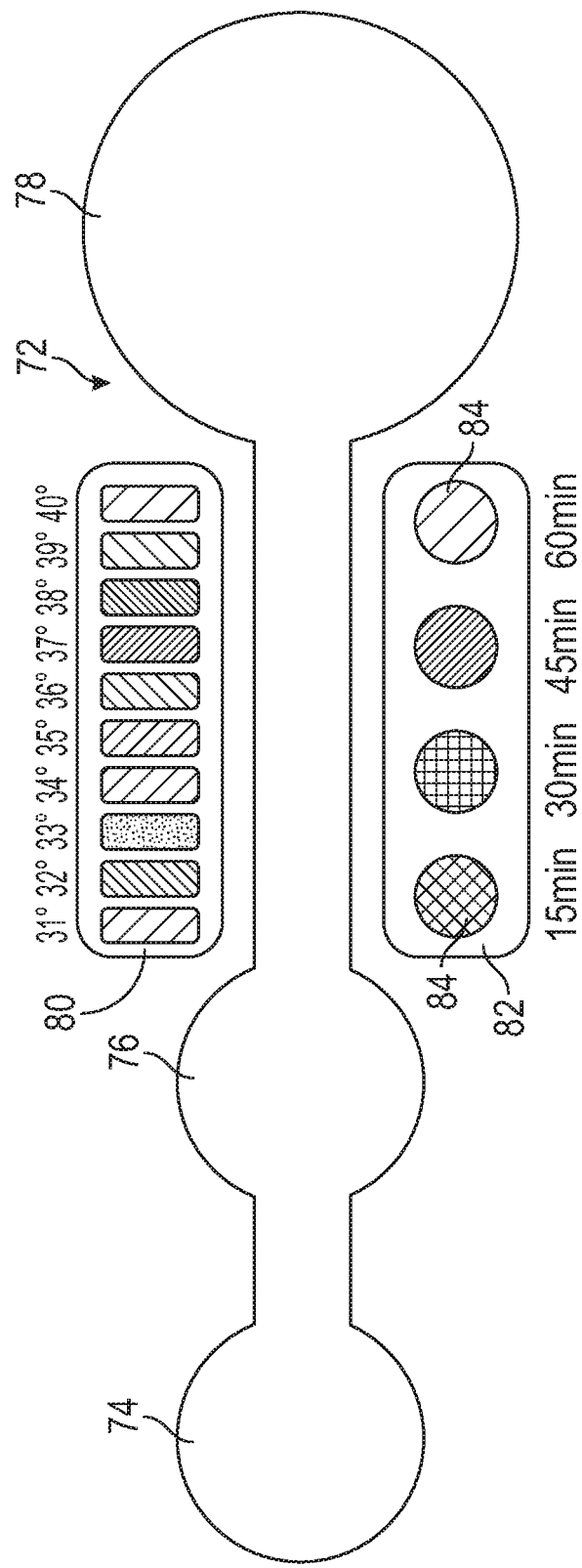
FIG. 13 is an enlarged plan view of a portion of a fourth embodiment of the sweat sensing device according to this invention showing a thermo-chromatic temperature indicator and an elapsed time indicator.

Referring now to FIG. 13, any of the sweat sensing devices 10, 50, 70, 100, and 120 disclosed herein may include the sweat channel 72 configured to measure temperature (also shown in FIG. 12). The sweat channel 72 includes the sweat inlet port 74 that extends through the lower layer 56 (see FIG. 12) and is in fluid communication with the second sweat channel 72. The color viewing window 78 is formed at a distal end of the second sweat channel 72, and the chloranilate mixing well 76 is formed intermediate the second sweat inlet port 74 and the color viewing window 78.

Figure 6:
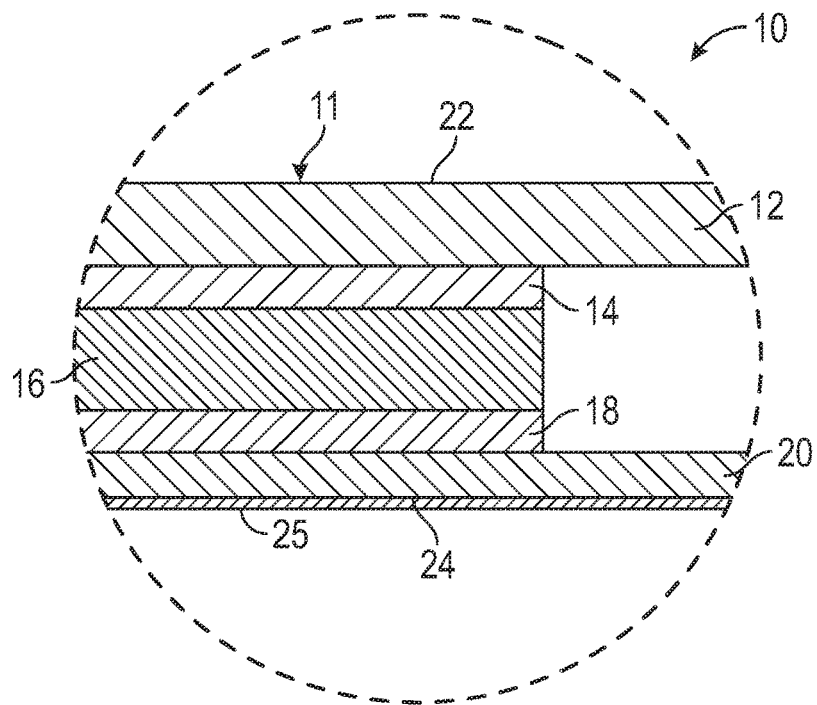
FIG. 6 is an enlarged cross-sectional view of the portion of the sweat sensing device within circle 6 of FIG. 5.
Figure 7:
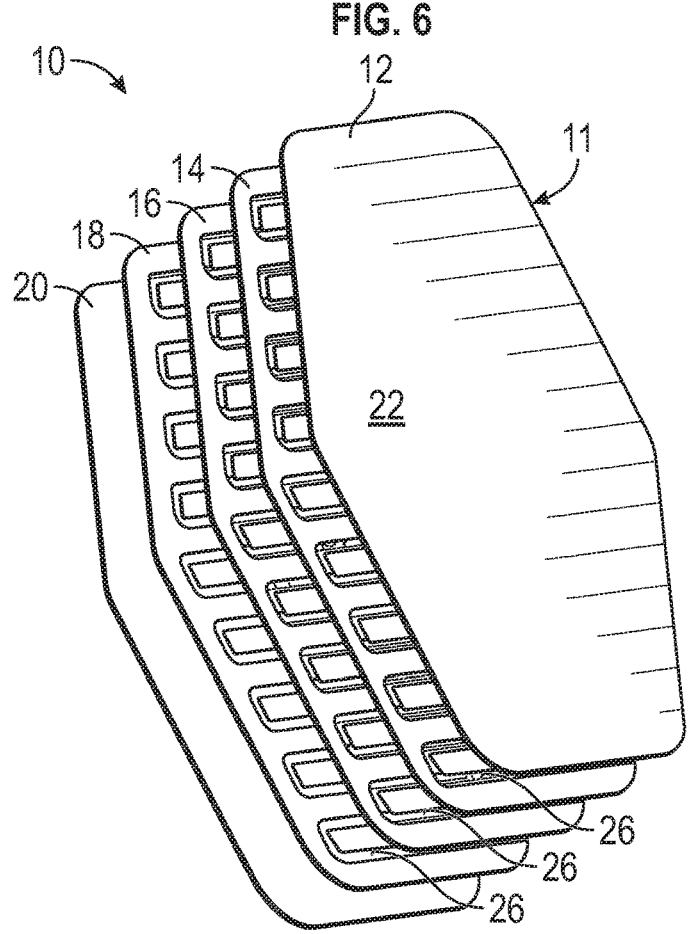
FIG. 7 is an exploded perspective view of the sweat sensing device illustrated in FIGS. 1 through 6.

In the illustrated embodiment, the chloranilate mixing well 76 includes an encapsulated thermochromic ink that is tuned to measure temperature. Examples of suitable thermochromic inks include, but are not limited to, inks having cholesteric and chiral nematic structures. The ink may be deposited directly between laminating layers of the sweat sensing devices 10, 50, 70, 100, and 120, such as between the second layer 14 and the fourth layer 18 as shown in FIG. 6, or between the first layer 12 and the fifth layer 20 in embodiment without the second layer 14 and the fourth layer 18. Alternatively, the sweat channel 72 may be formed in a pre-assembled, modular strip (not shown) and attached to the sweat sensing devices 10, 50, 70, 100, and 120.

The thermochromic ink will change color as the sweat temperature is increased, for example from colorless to red, orange, yellow, green, blue, and violet. Alternatively, a thermochromic ink may be selected that is temperature insensitive and will thus change color only at a pre-determined specific transition temperature. With such a temperature insensitive ink, when the sweat sensing device 10, 50, 70, 100, and 120 reaches the transition temperature, the thermochromic ink changes color.

The sweat channel 72 may also include an adjacent temperature indicator 80 that assigns a temperature value to a color as may appear in the color viewing window 78. If desired, the sweat channel 72 may also include an adjacent elapsed time indicator 82. The sweat inlet port 74 and the chloranilate mixing well 76 may be covered by a removable adhesive liner (not shown in FIG. 13, but similar to the liner 25), to cover sweat inlet port 74 and the chloranilate mixing well 76 and to hide the sweat, sweat-chloranilate mixture, and/or sweat-thermochromic ink mixture contained therein.

As shown in FIG. 13, oxidizing ink may be placed in a plurality of wells 84. When in use, the liner covering the elapsed time indicator 82 is removed, the wells 84 are exposed to air, and the inks begin to change color. The change in color of the ink may serve as an indicator of the time the sweat sensing device 10, 50, 70, 100, and 120 has been on the body. As shown, the elapsed time indicator 82 includes the plurality of wells 84, each with an ink formulation of increasingly slower reaction time, creating a graphic representation of time elapsed as shown at 82 in FIG. 13, i.e., circles having different colors at different time intervals. The oxidizing ink may be composed of polyphenol oxidase suspended in hydrogel or in cellulose. Inhibitors such as tentoxin or tropolone may be used to lengthen the duration of time before the ink changes color.

The removable adhesive liner (not shown) may cover the elapsed time indicator 82 and may have an oxygen scavenger, such as the oxygen scavenger 112 described below, attached to an inside surface thereof. When the removable adhesive liner (not shown) is applied to a sweat sensing device, it is positioned to cover and engage the elapsed time indicator 82 and prevents activation thereof. When the removable adhesive liner (not shown) is removed from the elapsed time indicator 82, the ink therein is exposed to oxygen and the colorimetric timer, i.e., the elapsed time indicator 82, is started.

In addition to the circles having different colors at different time intervals to represent elapsed time as shown at 82 in FIG. 13, the elapsed time indicator 82 may be configured as a word or words, dots, or other shapes that become visible over time. For example, the elapsed time indicator 82 may spell out the word "Expired" after a pre-determined period of time.

Alternatively, the elapsed time indicator 82 may include one or more conventional redox dye-based indicators, such as used for food packaging. One non-limiting example of such an indicator is the Ageless Eye®, produced by the Mitsubishi Gas Company.

Figure 14:
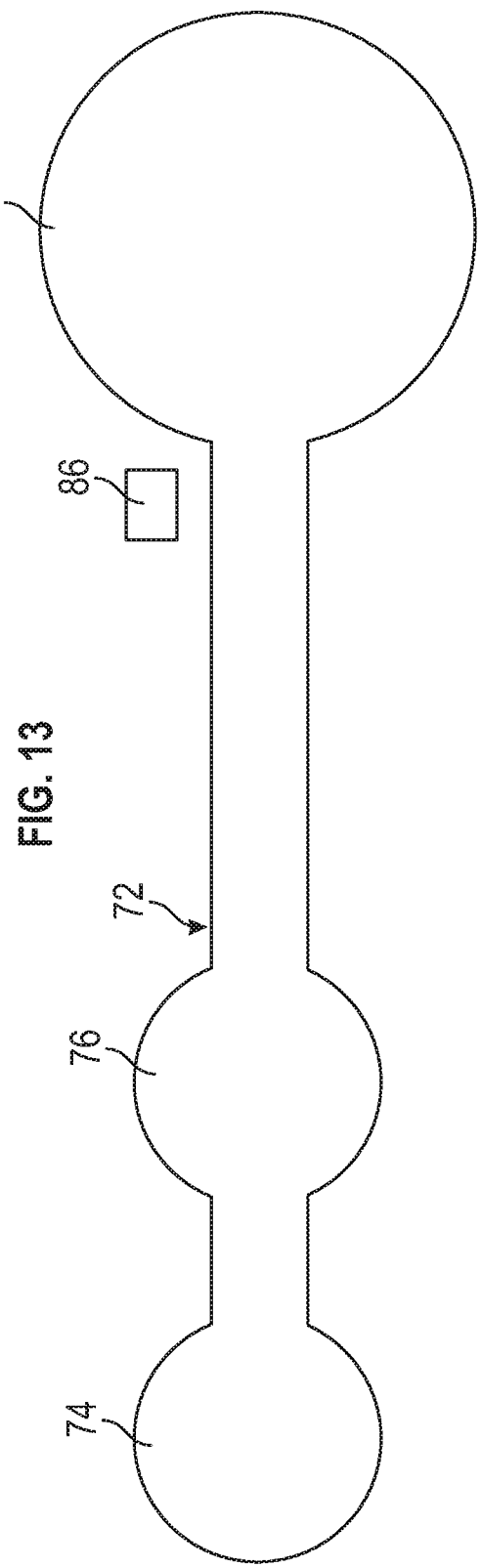
FIG. 14 is an enlarged plan view of a portion of a fifth embodiment of the sweat sensing device according to this invention showing an electronic temperature measurement and wear timer.

As shown in FIG. 14, the channel 72 may alternatively include an adjacent electronic device or sensor 86. Such a sensor 86 may be a temperature measurement and wear timer, such as an electronic device or any of the chemical sensors described herein. Additionally, the sensor 86 may be any other type of sensor, such as a timer or a sensor configured to detect a desired physiological parameter, such as ECG, PPG, heart rate, and respiration rate. The device or sensor 86 may also be configured to for wireless communication with the interactive console station 94 or the smartphone 96 in the wearable sweat monitoring system 90.

It will be understood that any of the sweat sensing devices 10, 50, 70, 100, and 120 described herein may have one or more the channels 72 formed therein, each of which may include the temperature indicator 80, adjacent elapsed time indicator 82, and or the sensor 86.

Figure 16:
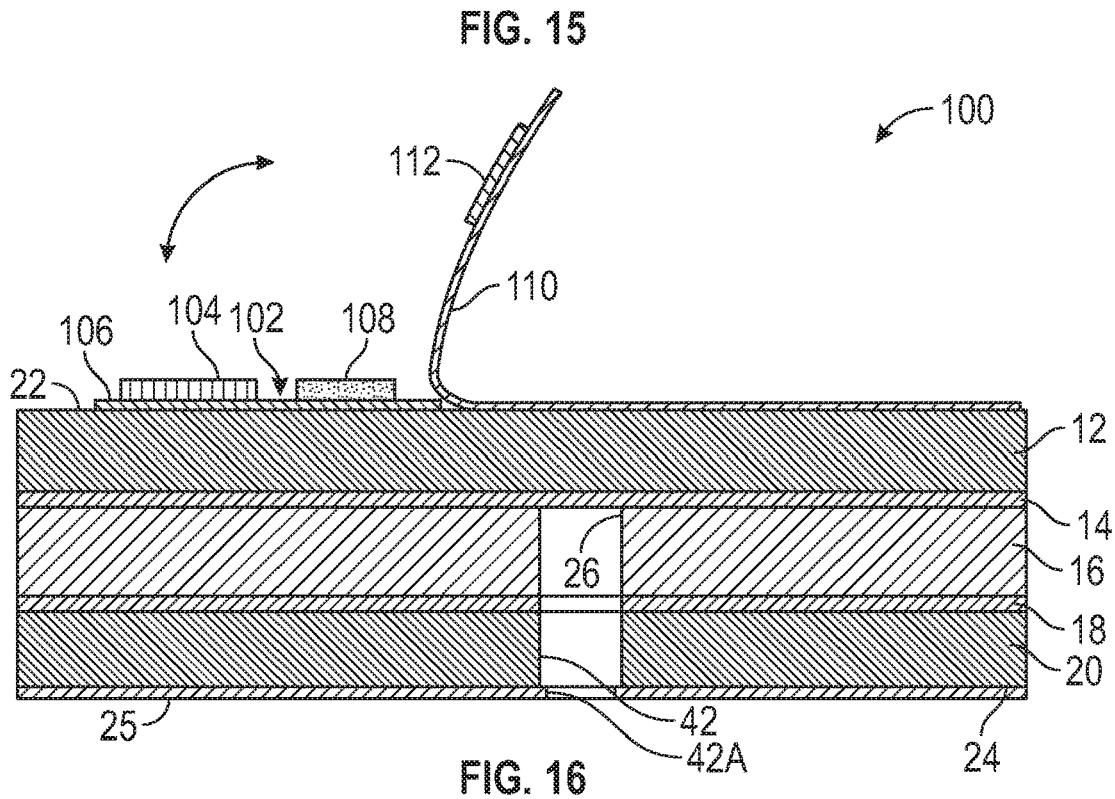
FIG. 16 is a cross-sectional elevational view of a sixth embodiment of the sweat sensing device according to this invention.

FIG. 16 is a cross-sectional elevational view of a sixth embodiment of the sweat sensing device 100. The sweat sensing device 100 is similar to the sweat sensing device 10 and includes the upper layer 12, the second layer 14, the third layer 16, the fourth layer 18, the lower layer 20, the outwardly facing surface 22, and the skin-facing surface 24. The sweat sensing device 100 also includes the sweat inlet port 42 in fluid communication with the sweat channel 26. An adhesive is applied to the skin-facing surface 24, and the skin-facing surface 24 is covered by the removable adhesive liner 25.

The sweat sensing device 100 may include a conventional flexible printed circuit board (PCB) 102 mounted to the outwardly facing surface 22. A battery, such as a zinc-air battery 104, an antenna, such as a near field communication (NFC) antenna 106, and a microprocessor 108 are operatively connected and mounted to the PCB 102.

A removable adhesive liner 110 may be attached to the outwardly facing surface 22 such that it covers the PCB 102. The illustrated removable adhesive liner 110 has the oxygen scavenger 112 attached to an inside surface thereof. The removable adhesive liner 110 may be formed from any desired material. When the removable adhesive liner 110 is applied to the outwardly facing surface 22, the oxygen scavenger 112 engages the zinc-air battery 104 and prevents activation thereof.

The microprocessor 108 may be any desired microprocessor, such as an NXP NHS3100 smart sensor with an embedded temperature sensor, or a Texas Instruments RF430FRL152 sensor transponder, which includes an integrated microcontroller and an analog to digital converter and temperature sensor. Additionally, the microprocessor 108 may be any microprocessor configured to have additional sensors attached thereto. For example, such additional sensors may include impedance, salinity, and pressure sensors (not shown). Advantageously, the NFC enabled integrated circuit devices may power themselves from the power harvested of the modulated 13.56 MHz current induced from an NFC-enabled smartphone 96 or tablet (not shown) in proximity of the sweat sensing device 100. When the smartphone 96 or tablet (not shown) is brought into proximity of the sweat sensing device 100, the sensors on the PCB 102 may measure the desired conditions of the sweat, e.g., temperature.

If desired, the microprocessor 108 may include a built-in clock/timer, and thus may record the time elapsed if the clock/timer is activated when the sweat sensing device 100 is applied to the skin of the user. For example, the NXP NHS3100 has a built in oscillator and memory register that may measure elapsed time beginning when the sweat sensing device 100 was applied and activated.

Another method of easily activating the clock/timer upon applying the sweat sensing device 100 to the user is with the zinc-air battery 104. When the removable adhesive liner 110 is applied to the outwardly facing surface 22, the oxygen scavenger 112 is positioned to engage the zinc-air battery 104 and prevent activation thereof.

The removable adhesive liner 25 must be removed before the sweat sensing device 100 may be applied to the skin of the user. When the user additionally removes the removable adhesive liner 110 from the outwardly facing surface 22, the zinc-air battery 104 is exposed to air, is activated, and thus provides power to the microprocessor 108, and any timer or sensor mounted thereon.

Figure 17:
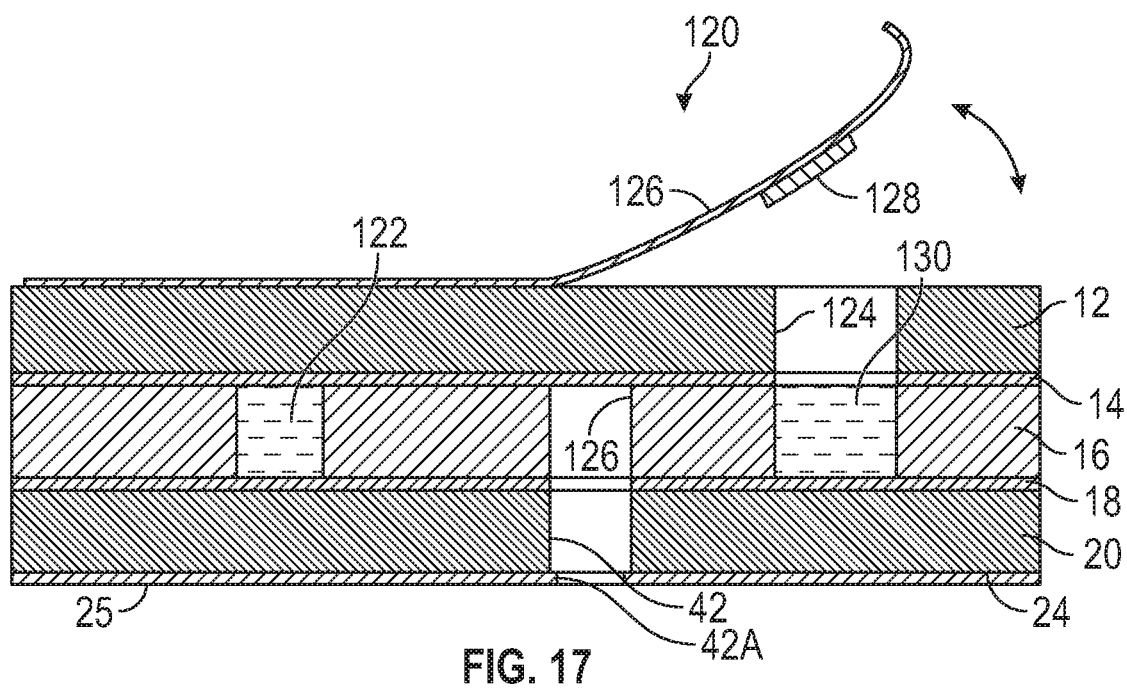
FIG. 17 is a cross-sectional elevational view of a seventh embodiment of the sweat sensing device according to this invention.

FIG. 17 is a cross-sectional elevational view of a seventh embodiment of the sweat sensing device 120. The sweat sensing device 120 is similar to the sweat sensing device 100 and includes the upper layer 12, the second layer 14, the third layer 16, the fourth layer 18, the lower layer 20, the outwardly facing surface 22, and the skin-facing surface 24. The sweat sensing device 110 also includes the sweat inlet port 42 in fluid communication with the sweat channel 26. An adhesive is applied to the skin-facing surface 24, and the skin-facing surface 24 is covered by the removable adhesive liner 25. In FIG. 17, the sweat sensing device 120 includes a chloranilate mixing well 122 having encapsulated thermochromic ink therein that is tuned to measure temperature, as described above. The sweat sensing device 120 also includes a well 124 covered by a removable adhesive liner 126 having an oxygen scavenger 128 attached to an inside surface thereof.

Oxidizing ink 130 may be placed in the well 124 defining a timer. When in use, the liner 126 is removed, the well 124 is exposed to air, allowing the ink 126 therein to begin to change color and thus starting the timer. The change in color of the ink serves as an indicator of the time the sweat sensing device 120 has been on the body. The oxidizing ink 130 may be one of the inks described herein above.

Advantageously, wearable sweat monitoring system 90 and the sweat sensing devices 10, 50, 70, 100, and 120 described herein provide an improved system and method for sweat based analysis and for applying this analysis to provide feedback to the user. This analysis and feedback may then be used to modify the operation or condition of one or more environments or systems based on one or more monitored, including but not limited to sweat volume loss, sweat rate loss, sweat electrolyte loss, sweat metabolite loss, and/or foreign chemicals/toxin concentrations in sweat.

As shown in FIG. 15, the sensed and collected condition information may be relayed to the interactive console station 94 and/or the smartphone 96 used to modify the operation of the wearable sweat monitoring system 90 and the environment in which the user is located. Additionally, a user may use the smartphone 96 to collect condition information and then relay that information to the interactive console station 94. The interactive console station 94 and the smartphone 96 may also be used independently of each other to collect condition information. For example, the sensed and collected condition information may cause an algorithm or computer program to be executed, e.g., started or stopped, or to change the flow of an executing program, function, or process.

A weighing station for example, may capture an image of the sweat sensing device 10, 50, 70, 100, or 120, analyze sweat volume, sweat rate, and electrolyte/metabolite loss information, and relay this information to a user, a patient, and/or a caregiver about fluid electrolyte and volume replenishment to replenish the users lost wet weight. Additionally, the sweat composition sensor, e.g., a chloride/sodium electrolyte sensor of the sweat sensing device 10, 50, 70, 100, or 120 may transmit a chloride concentration level to the interactive console station 94 and/or the smartphone 96, which may then make a virtual representation, e.g., an avatar, in a virtual environment exhibit the same or exaggerated dehydration characteristics of the user, such as an athlete.

Additionally, the sensed condition information collected by the wearable sweat monitoring system 90 may be used to modify the system output 98, for example by making a recommendation to alter a temperature, making a recommendation to alter a level of exertion, sending an alert to a caregiver or to emergency personnel, sending a signal that causes the room temperature to change to mitigate risks of dehydration or heat injury, sending a signal that activates a weighing station to measure heart rate or body temperature, and a signal that dims the lights or turns on a motorized fan in the user's environment causing the room temperature to change to mitigate further risks of dehydration or heat injury such as heat exhaustion.

Referring again to FIG. 15, the interactive console 94 may be any conventional interactive device or environment, including but not limited to a cloud server, a sports weighing station console, a virtual reality or augmented reality controller, a smart bottle sensor, and any device configured to provide feedback to the user, a coach, a medical professional, and the like.

In addition to recommending a specific electrolyte replenishment beverage or other nutrient, the wearable sweat monitoring system 90 may use the data collected from the sweat sensing devices 10, 50, 70, 100, and 120 to alter the lighting of a wirelessly enabled training room, change the temperature in a wirelessly enabled training room, recommend a new training regimen to the user, and provide other recommendations to modify the user's sweat rate, fluid intake, or environment based on the measured values. The information collected from the sweat sensing devices 10, 50, 70, 100, and 120 may also be used to ensure a safe operating environment by warning coaches, training staff, or medical professionals about electrolyte imbalances, injuries or possible injuries, cardiac conditions, and other potentially unsafe conditions for the user.

Advantageously, by using the wearable sweat monitoring system 90, one or more people may be monitored by one or more sweat sensing devices that indicate one or more conditions of the people to which the sweat sensing device or devices are attached. The conditions monitored and indicated may include physical conditions, such as location and motion of the person or a portion of the person's body. The conditions may also include physiologic or biologic conditions, such as the mechanical, physical, thermal and/or biochemical aspects of functions and/or processes of the person. The conditions may further include detection of chemical toxins, e.g., lead, mercury, and carcinogens, and stress biomarkers, e.g. cortisol, for mental, emotional, and psychiatric conditions, such as mood, focus, concentration, depression, and alertness.

The information monitored and indicated from one or more persons may be collected and processed or analyzed, and used as a direct input or used to select or modify an input to the interactive console station 94, or the smartphone 96 that controls the interactive environment experienced by the person. The interactive console station 94 and the smartphone 96 may use an integral or connected camera to take as input a picture and a color intensity of the sweat sensing devices 10, 50, 70, 100, and 120, and then uses this information to recommend a way to balance the missing nutrients, such as through fluid and nutrient replenishment, and/or to modify the environmental conditions, such as the temperature, humidity, background music, video, and lighting conditions.

The interactive console station 94 and the smartphone 96 may use one or more algorithms to determine whether to modify the environment or the operation of a system or machine. For example, the algorithm may use one or more detected physiologic or biometric conditions, such as sweat volume, sweat volume loss, sweat rate, sweat chloride loss, sweat sodium loss, sweat lactate loss, sweat electrolyte loss, sweat metabolite loss, sweat pH, sweat glucose, and foreign chemical and toxin concentrations in the sweat, or a rate of change of these detected physiologic or biometric conditions, to then influence or modify the operation of the interactive console station 94 and/or the smartphone 96

The algorithm may, for example, provide information about diet, modifying intensity of training, meditation routines to control breathing, or modifications in sports hydration drink intake, including providing a personalized electrolyte recipe for the user to replenish lost nutrients. Additionally, the algorithm may compare one or more parameters representative of one or more sensed conditions to a predefined threshold value, a range of values, or a previous recorded value for an athlete and/or a team to compare past performance or population datasets.

The interactive console station 94 and/or the smartphone 96 may have image correction algorithms to correct for the effects of shadowing, glare, brightness variations, and specular reflections on the outwardly facing surfaces of the sweat sensing devices 10, 50, 70, 100, and 120, such as the outwardly facing surface 22. The sweat sensing devices 10, 50, 70, 100, and 120 may include indicia imprinted on the polymer layer (not shown) that may be laminated to the outwardly facing surfaces thereof. The indicia may include color calibration landmarks used to subtract the effects of disparate lighting conditions and the effects of shadows. The image processing and analysis of the outwardly facing surfaces of the sweat sensing devices 10, 50, 70, 100, and 120 results in a measurement of sweat volume and chloride concentration, which may be relayed back to the user or may be applied as an input to change recommend a change to the surrounding environment. The indicia may also include any work or work or symbol, such as a brand name or trademark.

The sweat sensing devices 10, 50, 70, 100, and 120 may also contain embedded thin film electronics modules or devices for sensing, power management, and wireless communication, such as for example, the NFC antenna 106, or a Bluetooth® device. These electronics devices may be packaged or bare-die electronics parts and may be embedded within the inner layers, such as the second, third, and fourth layers 14, 16, and 18, respectively, thereby providing a moisture barrier to protect the electronics devices.

An image of part or all of the outwardly facing surface of the sweat sensing devices 10, 50, 70, 100, and 120 may be used to quantify the volume of sweat collected and the rate of sweat production. Sweat volume may be determined by measuring the distance of sweat propagation along a sweat channel, such as the sweat channel 26, and converting distance to volume using the known channel geometry of a given sweat sensing device. Volumetric sweat rate as a function of time, e.g., liters per hour, may optionally be determined from any of the embodiments of the sweat sensing devices 10, 50, 70, 100, and 120 described herein, if the time at which the sweat sensing device was applied to the skin is known.

In accordance with some embodiments of the invention, a whole-body sweat volume and/or whole-body sweat rate may be quantified from the sweat sensing device. If the sweat sensing device is attached to the skin of the user and the sweat collection area is known, the sweat volume, measured as described above, may be extrapolated to a whole-body sweat volume. If desired, information about the location of the sweat sensing device on the wearer's body and/or the sweat characteristics of the wearer may be used to extrapolate the whole-body sweat volume.

As described above, the presence and concentration of various biochemical components of sweat may be measured colorimetrically on the improved sweat sensing device 10, 50, 70, 100, and 120. The color and/or color change measured may be introduced or generated by a chemical reaction that is known to indicate the biochemical component of interest.

The color of the sweat in the sweat channels and the various assay wells may be measured relative to one or more reference colors on the sweat sensing device 10, 50, 70, 100, and 120. These reference colors may include, but are not limited to, colors printed on the sweat sensing device 10, 50, 70, 100, and 120 before, during, or after manufacture, colors generated by the sweat sensing device 10, 50, 70, 100, and 120 as a result of fluid flow, and colors present in the ambient environment around the sweat sensing device 10, 50, 70, 100, and 120. Colorimetric measurements may also use any relevant information about the measurement system, including, but not limited to, sensor type, color sensitivity, exposure time, focal distance, and depth of focus.

Because of the relatively small size of the sweat sensing devices 10, 50, 70, 100, and 120 and the fluid flow channels therein, sweat measurements are performed on time-limited samples of sweat by collecting restricted volumes of sweat in isolated regions, i.e., the sweat channels, of the sweat sensing device 10, 50, 70, 100, and 120. The measurement area may allow measurement of electrical impedance of the sweat in the capture volume.

As noted above, the sweat channels described herein may be variously formed in the second layer 14, the third layer 16, and in the fourth layer 18, or in combinations of layers, such as in the second and third layers 14 and 16 and in the third and fourth layers 16 and 18. By spacing areas of increase height at pre-determined intervals in the sweat channel a fluid flow rate can be determined as the fluid in the channel travels between each area of increased channel height, and thus between areas wherein the color change within the sweat channel may be more easily seen because a larger volume of dye therein may appear darker.

The rate of flow of sweat past a measurement area, such as any pre-determined and identified region of interest on the sweat sensing devices 10, 50, 70, 100, and 120 is controlled to ensure that any colorimetric, electrical, or other means of measurement reaches an equilibrium state while the sweat is still in the measurement area, i.e., that any reaction between sweat and an assay within the region is fully complete and or dye used therein is evenly diffused.

The sweat sensing device 10, 50, 70, 100, and 120 measures sweat rate and biochemical composition as a function of time. A sweat rate may be measured as a function of time by measuring sweat volume at predetermined time intervals. Biochemical composition may be measured as a function of time by measuring limited-volume sweat samples collected over a known time period.

The sweat sensing devices 10, 50, 70, 100, and 120 may be adhered to the forearm, head, shoulders, arms, hands, torso, chest, legs and feet of the user.

The sweat sensing device 10, 50, 70, 100, and 120 may detect and measure the rate of sweat loss, sweat composition, and chemical toxin and/or metabolite levels in sweat. Once the detection and measurement is completed, sweat sensing device 10, 50, 70, 100, and 120 may be peeled off of the skin and discarded.

Preferably, the chemicals deposited in the biochemical assay wells chemical assays are positioned therein to ensure optimal reaction conditions for the sweat as it flows through the sweat channel. Depositing chemicals within biochemical assay wells having relatively large surface areas, such as a diameter within about 0.020 in to about 0.200 in ensures optimal exposure to sweat and increases the likelihood of reaction with electrolytes in the sweat. Increasing the surface area of contact between the chemicals in the biochemical assay wells increases the chemical reaction with the sweat and thereby helps overcome the diffusion time constant limitations.

The colorimetric information on the sweat sensing device 10, 50, 70, 100, and 120 may be analyzed by algorithms within the interactive console station 94 and/or the smartphone 96, and a recommendation, such as the most suitable electrolyte infused drink to be consumed, may be displayed back to the user via the smartphone 96 or a display screen of the interactive console station 94.

Additionally, the colored dyes used in the sweat sensing device 10, 50, 70, 100, and 120 may be customized and personalized by depositing specific colored dyes in the sweat channels to match the fluid color of a specific sports drink. For example, a blue colored sports drink may be matched with a sensing device having a blue colored dye deposited in the sweat channel.

The interactive console station 94 and/or the smartphone 96 may also be connected to lighting control, thermostat control, music control, and video control systems. Thus, the feedback from the sweat sensing device 10, 50, 70, 100, and 120 may provide inputs for controlling these environment control systems.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A sweat sensing device comprising:
a flexible body having a first, outwardly facing surface and a second, skin facing surface;
a first sweat channel formed in the body, the first sweat channel having a first end defining a fluid inlet and a second end, and a biochemical assay well formed in the first sweat channel;
an assay material disposed in the biochemical assay well of the first sweat channel, the assay material positioned to react with sweat traveling through the sweat channel and to provide one of a visual indicator and an indicator detectable by a camera and connected processor of the flow of the sweat in the sweat channel; and
a second sweat channel formed in the body, the second sweat channel including a first end defining a fluid inlet and a second end, a color viewing window formed in the second sweat channel, and a biochemical assay well formed in the second sweat channel between the first end and the color viewing window;
wherein the biochemical assay well of the second sweat channel defines a chloranilate mixing well, the sweat sensing device further including chloranilate disposed in the biochemical assay well, and wherein the chloranilate is suspended in a suspension of one of p-HEMA and polyethylene glycol, the color viewing window positioned to collect sweat that has passed through and reacted with the chloranilate in the biochemical assay well, and to provide one of a visual indicator and an indicator detectable by a camera and connected processor of a color of the sweat and chloranilate in the color viewing window.

2. The sweat sensing device according to claim 1, wherein the flexible body is formed from three layers of material bonded together, and wherein the sweat channel is formed in an inner layer of the three layers.

3. The sweat sensing device according to claim 1, wherein the flexible body is formed from five layers of material bonded together, and wherein the sweat channel is formed in one of one of three inner layers of the five layers and a plurality of any of the three inner layers of the five layers.

4. The sweat sensing device according to claim 1, wherein the second end of the sweat channel defines a fluid outlet.

5. The sweat sensing device according to claim 1, including a plurality of the second sweat channels, each of the plurality of second sweat channels having a different assay material disposed in its biochemical assay well.

6. The sweat sensing device according to claim 5, wherein the assay materials are chosen to detect one of physiologic and a biometric condition in the sweat in the second sweat channel, the physiologic and a biometric conditions selected from the group consisting of sweat volume, sweat volume loss, sweat rate, sweat chloride loss, sweat sodium loss, sweat lactate loss, sweat electrolyte loss, sweat metabolite loss, sweat pH, sweat glucose, and foreign chemical and toxin concentrations in the sweat.

7. A sweat monitoring system comprising:
a sweat sensing device configured to be adhered to the skin of a user to collect sweat and detect one of physiologic and a biometric condition selected from the group consisting of sweat volume, sweat volume loss, sweat rate, sweat chloride loss, sweat sodium loss, sweat lactate loss, sweat electrolyte loss, sweat metabolite loss, sweat pH, sweat glucose, and foreign chemical and toxin concentrations in the sweat;
an interactive console station having a connected camera;
wherein the camera of the interactive console station captures an image of the sweat sensing device and generates an output to the user via the interactive console station;
a smartphone having a camera, wherein the smartphone camera captures an image of the sweat sensing device and generates an output to the user via one of the interactive console station and the smartphone display screen;
wherein the image of the sweat sensing device is captured a plurality of times while the sweat sensing device is being worn and adhered to the skin of the user;
wherein a processor in one of the interactive console station and the smartphone uses one or more algorithms to generate the output;
wherein the output is one of a recommendation of a specific formulation of electrolytes, carbohydrates, and fluids to consume to achieve electrolyte and metabolite balance in the user, a recommendation to consume specific nutrients, a recommendation to alter a temperature, a recommendation to alter a level of exertion, an alert to a caregiver, and alert to emergency personnel, a signal that causes the room temperature to change to mitigate risks of one of dehydration and heat injury, a signal that activates a weighing station to measure one of heart rate and body temperature, and a signal that one of dims the lights and turns on a motorized fan in the user's environment;
wherein the output and recommendations communicated to the user via one of the smartphone and the interactive console station;
wherein the sweat sensing device includes a flexible body formed from five layers of material bonded together and having:
a first, outwardly facing surface;
a second, skin facing surface;
a first sweat channel formed in the body, the first sweat channel having a first end defining a fluid inlet and a second end, wherein the first sweat channel is formed in one of one of three inner layers of the five layers and a plurality of any of the three inner layers of the five layers, a biochemical assay well formed in the first sweat channel, and an assay material disposed in the biochemical assay well, the assay material positioned to react with sweat traveling through the sweat channel and to provide one of a visual indicator and an indicator detectable by a camera and connected processor of the flow of the sweat in the sweat channel; and
a second sweat channel formed in the body, the second sweat channel having a first end defining a fluid inlet and a second end, a color viewing window formed in the second sweat channel, a biochemical assay well formed in the second sweat channel between the first end and the color viewing window, and chloranilate disposed in the biochemical assay well, wherein the chloranilate is suspended in a suspension of one of p-HEMA and polyethylene glycol, and wherein the color viewing window is positioned to collect sweat that has passed through and reacted with the chloranilate in the biochemical assay well, and to provide one of a visual indicator and an indicator detectable by a camera and connected processor of a color of the sweat and chloranilate in the color viewing window.

8. The sweat monitoring system according to claim 7, wherein the sweat monitoring system includes a plurality of the sweat sensing devices configured to be adhered to the skin of a user to collect sweat and detect one of the physiologic and a biometric conditions.

9. The sweat monitoring system according to claim 7, including a plurality of the second sweat channels, each of the plurality of second sweat channels having a different assay material disposed in its biochemical assay well;
  wherein the assay materials are chosen to detect one of physiologic and a biometric condition in the sweat in the second sweat channel, the physiologic and a biometric conditions selected from the group consisting of sweat volume, sweat volume loss, sweat rate, sweat chloride loss, sweat sodium loss, sweat lactate loss, sweat electrolyte loss, sweat metabolite loss, sweat pH, sweat glucose, and foreign chemical and toxin concentrations in the sweat.

* * * * *